United States Patent [19]

Behling et al.

[11] Patent Number: 4,994,094
[45] Date of Patent: Feb. 19, 1991

[54] METHOD OF REMOVING ORGANIC COMPOUNDS FROM AIR/PERMANENT GAS MIXTURES

[75] Inventors: Dieter Behling, Hamburg; Karl Hattenbach; Klaus Ohlrogge, both of Geesthacht; Klaus-Victor Peinemann, Reinbek; Jan Wind, Barsbüttel, all of Fed. Rep. of Germany

[73] Assignee: GKSS Forschungszentrum Geesthacht GmbH, Geesthacht, Fed. Rep. of Germany

[21] Appl. No.: 316,054

[22] Filed: Feb. 24, 1989

[30] Foreign Application Priority Data

Feb. 26, 1988 [DE] Fed. Rep. of Germany ....... 3806107

[51] Int. Cl.$^5$ .................. B01D 53/22; B01D 71/64
[52] U.S. Cl. ............................ 55/16; 55/68; 55/74
[58] Field of Search ............. 55/16, 158, 25, 26, 55/62, 68, 74; 585/818, 819

[56] References Cited

U.S. PATENT DOCUMENTS

| | | | |
|---|---|---|---|
| 2,159,434 | 5/1939 | Frey | 55/16 X |
| 2,388,095 | 10/1945 | Stahly | 55/16 |
| 2,540,151 | 2/1951 | Weller et al. | 55/16 |
| 2,617,493 | 11/1952 | Jones | 55/16 |
| 3,930,814 | 1/1976 | Gessner | 55/16 |
| 4,051,372 | 9/1977 | Aine | 55/158 X |
| 4,104,037 | 8/1978 | Garrett et al. | 55/16 |
| 4,119,417 | 10/1978 | Heki et al. | 55/16 X |
| 4,140,499 | 2/1979 | Ozaki et al. | 55/16 X |
| 4,264,338 | 4/1981 | Null | 55/158 X |
| 4,374,657 | 2/1983 | Schendel et al. | 55/16 X |
| 4,386,944 | 6/1983 | Kimura | 55/16 |
| 4,553,983 | 11/1985 | Baker | 55/16 |
| 4,639,257 | 1/1987 | Duckett et al. | 55/16 |
| 4,673,418 | 6/1987 | Peinemann | 55/158 |
| 4,690,695 | 9/1987 | Doshi | 55/16 |
| 4,772,295 | 9/1988 | Kato et al. | 55/16 |
| 4,818,452 | 4/1989 | Kneifel et al. | 55/158 X |

FOREIGN PATENT DOCUMENTS

| | | | |
|---|---|---|---|
| 0110858 | 6/1984 | European Pat. Off. | 55/16 |
| 62-286517 | 12/1987 | Japan | 55/158 |

*Primary Examiner*—Robert Spitzer
*Attorney, Agent, or Firm*—Robert W. Becker & Associates

[57] ABSTRACT

A method of removing organic compounds from an air/permanent gas mixture. This mixture, as untreated medium, is conveyed to a first gas separation membrane and is divided into a filtrate gas stream that is concentrated with organic compounds and a retained gas stream that is depleted of organic compounds. The concentrated filtrate is conveyed to a recovery device for the recovery of organic compounds therefrom. The pressure of the air/permanent gas mixture is raised prior to entry thereof into the first gas separation membrane. The pressure of the concentrated filtrate is reduced after exit thereof from the first gas separation membrane. The depleted gas stream is discharged into the atmosphere, and the gas stream that exits the recovery device is returned to the air/permanent gas mixture at some point subsequent to the pressure increase thereof.

18 Claims, 7 Drawing Sheets

Flux Density vs Temperature (P = 1230 mbar)

n - Butane Flux Density vs Pressure

Propane Flux Density vs Pressure

Gas fluxes through two types of polyetherimide / silicone rubber composite membranes

METHOD OF REMOVING ORGANIC COMPOUNDS FROM AIR/PERMANENT GAS MIXTURES

BACKGROUND OF THE INVENTION

1. Field of the Invention

The present invention relates to a method of removing organic compounds from an air/permanent gas mixture, including conveying said air/permanent gas mixture (untreated medium) to a first gas separation membrane means and dividing said mixture into a gas stream (filtrate) that is concentrated with organic compounds and a gas stream (retained gas) that is depleted of organic compounds, with the concentrated filtrate gas stream being conveyed to a recovery device for the recovery of said organic. compounds therefrom.

2. Description of the Prior Art

In a known method of this type (U.S. Pat. 4,553,983 Baker dated Nov. 19, 1985 ), an exhaust air mixture that is to be separated, and that is at a high temperature, is conveyed to a furnace that is connected with a mixture-feed portion of the membrane means. The retained gas is again introduced into the furnace and is mixed with the exhaust air mixture that is to be separated and that is conveyed, as mentioned previously, to the furnace, and is again conveyed to the membrane means. The filtrate that is concentrated with organic compounds is conveyed to a compressor and subsequently to a recovery device, which is embodied as a condensor and from which the condensed organic compound exists. The exhaust air that leaves the recovery device is either conveyed directly to the atmosphere or is again conveyed to the furnace together with the retained gas coming from the gas separation membrane means.

Generally true is that the gas transport through a gas separation membrane is proportional to the transmembrane partial pressure difference. The separating capacity of a gas separation membrane, and hence the purity of the filtrate that is generated, is essentially a function of the pressure on the front side of the membrane to the filtrate pressure, i.e. the ratio of the retained gas pressure to the filtrate pressure. A gas separation membrane, in other words a method utilizing such a gas separation membrane, operates optimally only if not only a high inlet pressure as well as a pressure ratio adapted to the selectivity of the gas separation membrane can be established.

The drawback of this known method is essentially that these criteria can be fulfilled only at relatively low concentrations of organic compounds in air/permanent gas mixtures, so that this known method has the particular drawback that the exhaust air thereof still contains a high concentration of organic compounds. For example, this known method cannot maintain levels prescribed by regulations in the Federal Republic of Germany for the maximum organic compound content in the exhaust air of industrial plants.

Furthermore, there is a great need to provide a method with which, for example in connection with the continuously scarcer raw material resources on the one hand and the increased environmental awareness on the other hand, the fraction of the organic compounds from the considerable quantities of air/gaseous petroleum derivatives that form in petroleum tanks can again be condensed and utilized, and not be released into the environment.

It is therefore an object of the present invention to provide a method with which, without the need for much intrinsic energy, an optimum amount of organic compounds can be removed from an air/permanent gas mixture, with which the gas mixture discharged into the environment contains such a low proportion of organic compounds that prescribed values for foreign gas fraction can be maintained, with which little expense for apparatus is required, and which functions without difficulties eve when the concentrations of organic compounds in the air/permanent gas mixture (untreated medium) are high.

BRIEF DESCRIPTION OF THE DRAWINGS

This object, and other objects and advantages of the present invention, will appear more clearly from the following specification in conjunction with the accompanying schematic drawings, in which.

SUMMARY OF THE INVENTION

Figure 1:
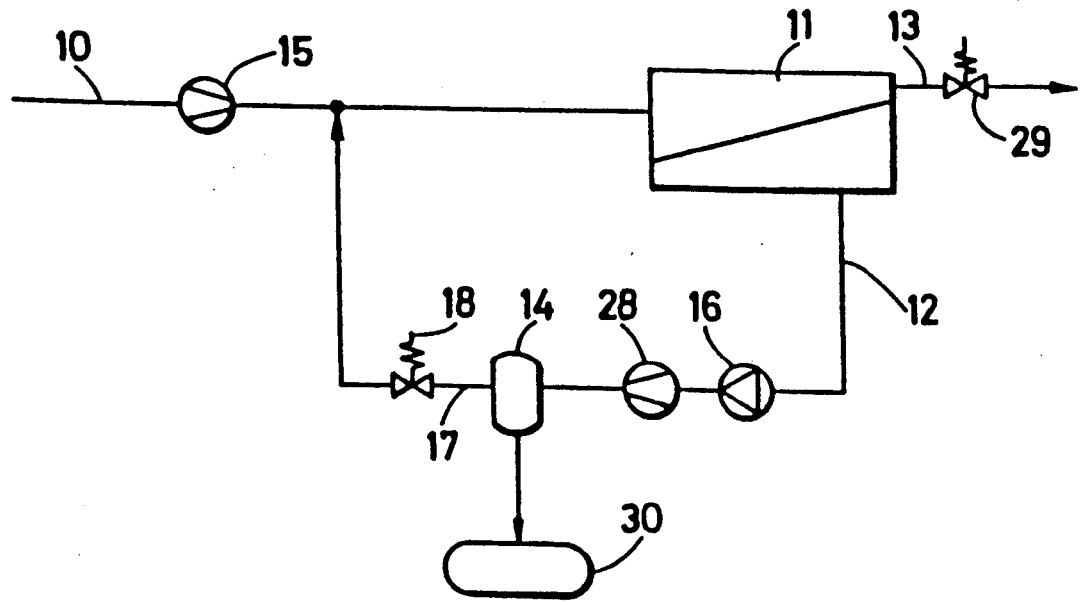
FIG. 1 is a view that shows a first exemplary embodiment of an arrangement for carrying out the inventive method.

The method of the present invention is characterized primarily by: raising the pressure of the primary air/permanent gas mixture prior to entry thereof into the first gas separation membrane means; reducing the pressure of the concentrated filtrate gas stream after exit thereof from the first gas separation membrane means; discharging the depleted gas stream that leaves the first gas separation membrane means into the atmosphere; and returning the gas stream or exhaust air that exits from the recovery device to the air/permanent gas mixture at a point subsequent to where the pressure of this mixture has been raised.

The advantage of the inventive proposal is essentially that on the one hand high concentrations of organic compounds in air/permanent gas mixtures can be removed, since the pressure gradient between the upper and lower sides of the membrane, which pressure gradient is important for an optimum separation effect, is established pursuant to the present invention by increasing the pressure of the primary air/permanent gas mixture prior to its entry into the gas separation membrane, and the pressure of the concentrated gas stream is reduced in a predetermined manner after exit thereof from the gas separation membrane.

Pursuant to one advantageous specific embodiment of the present invention, the exhaust air gas stream that exits the recovery device is again conveyed to the primary air/permanent gas mixture immediately prior to entry thereof into the gas separation membrane, so that a residual fraction of organic compounds that remains in the exhaust air can again be conveyed to the gas separation membrane and is not discharged into the atmosphere, as occurs, for example, with the heretofore known method.

The pressure of the exhaust air that exits the recovery device is advantageously reduced, i.e. is depressurized to such an extent that it is at essentially the same pressure as the air/permanent gas mixture that is directly entering the gas separation membrane.

Pursuant to another specific embodiment of the inventive method, the exhaust air gas stream that exits the recovery device is conveyed to a second gas separation membrane, the depleted gas stream of which is conveyed to the atmosphere and the concentrated gas stream of which is combined directly with the concentrated gas stream that exits the first gas separation membrane. In order to be able to set the operating pressure of the second gas separation membrane, the pressure of the gas stream leaving the latter is preferably adjustable. This embodiment of the inventive method makes it possible with simple means to provide a further separation for the exhaust air gas stream that exits the recovery device, in other words, splitting of this gas stream into a concentrated gas mixture that is returned to the recovery device, and an improved purifying of the retained gas mixture to a desired exhaust air concentration for discharge into the environment.

Pursuant to a further specific embodiment of the present invention, the higher pressure primary air/permanent gas mixture is conveyed to a third gas separation membrane, the oxygen-depleted gas stream of which enters the first gas separation membrane, and the oxygen-rich gas stream of which is conveyed to the atmosphere, with the third gas separation membrane having increased oxygen-passing characteristics. In this third gas separation membrane, for example and oxygen/nitrogen ratio, if this gas separation membrane has a special oxygen/nitrogen selectivity, is shifted on the filtrate side to the favor of the oxygen, so that an oxygen-depleted gas stream already enters the first original gas separation membrane, i.e. a concentrated filtrate is conveyed to the first gas separation membrane.

Pursuant to another specific embodiment of the inventive method, the concentrated gas stream, prior to entry into the recovery device, is conveyed to a third gas separation membrane, the oxygen-depleted gas stream of which is conveyed to the recovery device, and the oxygen-rich gas stream of which is conveyed to the atmosphere, with the third gas separation membrane having increased oxygen-passing characteristics. This embodiment is used in particular to avoid a build-up of oxygen in the recovery cycle. This step is particularly economical if the recovery device is operated under pressure, i.e. the recovery is effected under pressure and the pressure is used for both gas separation membranes.

The previously described advantageous configuration of a further specific embodiment of the inventive method can additionally be advantageously modified by conveying the exhaust air that exits the recovery device to a third gas separation membrane, the oxygen-depleted gas stream of which is conveyed to the second gas separation membrane, and the oxygen-rich gas stream of which is conveyed to the atmosphere, with the third gas separation membrane having increased oxygen-passing characteristics. This embodiment of the inventive method is also used to avoid a build-up of the oxygen, so that in this case also the method can be operated in a particularly economical manner.

Pursuant to a final advantageous specific embodiment of the inventive method, the depleted gas stream that exits the second gas separation membrane is utilized prior to being discharged into the atmosphere, for driving a pump mechanism, with the oxygen-rich gas stream of the third gas separation membrane being conveyed to the suction or intake side of the pump mechanism to produce a partial vacuum of the gas stream. Also in this manner, the operating pressure of the second gas separation member c an advantageously be established, instead of via a pressure regulator, via the depleted gas stream that exits the second gas separation membrane, and the pressure for operating the third gas separation membrane can again thereby be used for separating organic compounds with the aid of the pump mechanism to generate a partial vacuum on the oxygen-rich side (filtrate side of the oxygen separation membrane) of the third gas separation membrane.

Advantageously, with all of the aforementioned embodiments of the inventive method the lower pressure concentrated gas stream that leaves the first gas separation membrane device has the pressure thereof increased prior to entry into the recovery device, since in this way the recovery device can operate more effectively.

Similarly, with all of the aforementioned advantageous embodiments of the present invention, the pressure of the depleted gas stream can be reduced after exiting the first gas separation membrane and prior to be discharged into the atmosphere. The adjustment of the pressure of the retained gas is made possible by a direct adaptation of the pressure conditions in conformity with the selectivity of the gas separation membrane.

The recovery of the organic compounds from the concentrated gas stream in the recovery device can advantageously be effected by the withdrawal of heat, condensation under pressure, or also via sorption. It is also advantageously possible to utilize any desired combinations of the aforementioned types of recovery of the organic compounds in a recovery device. The sorption can, for example, be a physical absorption, a chemical absorption, or also adsorption.

The gas separation membrane can preferably be a polyetherimide composite membrane, with this being particularly applicable for the first and second gas separation membranes.

For the third gas separation membrane, an asymmetrical polyetherimide membrane is preferably used since it has a higher oxygen/hydrocarbon selectivity. Finally, with certain embodiments of the inventive method it is advantageous to make the air/permanent gas mixture that is to be separated inert prior to increasing the pressure thereof in order to largely prevent the formation of an explosive mixture as a result of the increase in pressure.

Further specific features of the present invention will be described in detail subsequently.

DESCRIPTION OF PREFERRED EMBODIMENTS

Referring now to the drawings in detail, a first arrangement for carrying out the inventive method is illustrated in FIG. 1 and will be described subsequently. Via an untreated gas line 10, an air/permanent gas mixture (untreated medium) that contains organic compounds is supplied to a compressor 15. In a first gas separation diaphragm device 11, the untreated medium is separated into a gas stream 13 (retained gas) that is depleted of organic compounds, and a gas stream 12 (filtrate) that is concentrated with organic compounds. The filtrate 12 is conveyed to a recovery device 14 via a vacuum pump 16, and from there via compressor 28. In the recovery device 14, the organic compounds in the filtrate 12 are condensed by pressure, the removal of heat, adsorption, or a combination of these removal means, and are conveyed to a tank 30. With the aid of a pressure regulator 18, the exhaust air 17 from the recovery device 14 is depressurized to the pressure of the compressor 15 and is mixed with the higher pressure air/permanent gas mixture 10 (untreated medium). The flow through the gas separation diaphragm or membrane 11 is set or adjusted with the aid of a pressure regulator 29. In the arrangement illustrated in FIG. 2 for carrying out the method of the present invention, an air/permanent gas mixture 10 (untreated medium) that contains organic compounds is again conveyed via an untreated gas line 10 to a compressor 15. In the gas separation membrane device 11, the untreated medium 10 is split into a gas stream 13 (retained gas) that is depleted of organic compounds, and a gas stream 12 (filtrate) that is concentrated with organic compounds. The filtrate 12 is conveyed to a recovery device 14 via a vacuum pump 16 and a compressor 28. Disposed downstream of the recovery device 14 is a second gas separation membrane device 19. Utilizing the elevated inlet pressure, the exhaust air 17 that leaves the recovery device 14 is split into a depleted gas stream 20 (retained gas) having a low constant of organic compounds, and a concentrated gas stream 21 (filtrate). The concentrated gas stream 21 (filtrate) is mixed with the filtrate 12 of the first gas separation membrane device 11. The operating pressure of the second gas separation membrane device 19 is set or adjusted via a pressure regulator 22. The depleted gas stream 20 (retained gas), which in effect forms the exhaust air of the second gas separation membrane device 19, is mixed with the retained gas 13, i.e. the exhaust air 13, of the first gas separation membrane device 11. The condensed organic compounds recovered in the device 14, which compounds can basically be recovered in the same manner as with the arrangement of FIG. 1, are conveyed to the tank 30. Also with this embodiment of the inventive method, the flow rate of the air/permanent gas mixture 10 (untreated medium) through the first gas separation membrane device 11 is set o adjusted with the aid of the pressure regulator 29.

Figure 2:
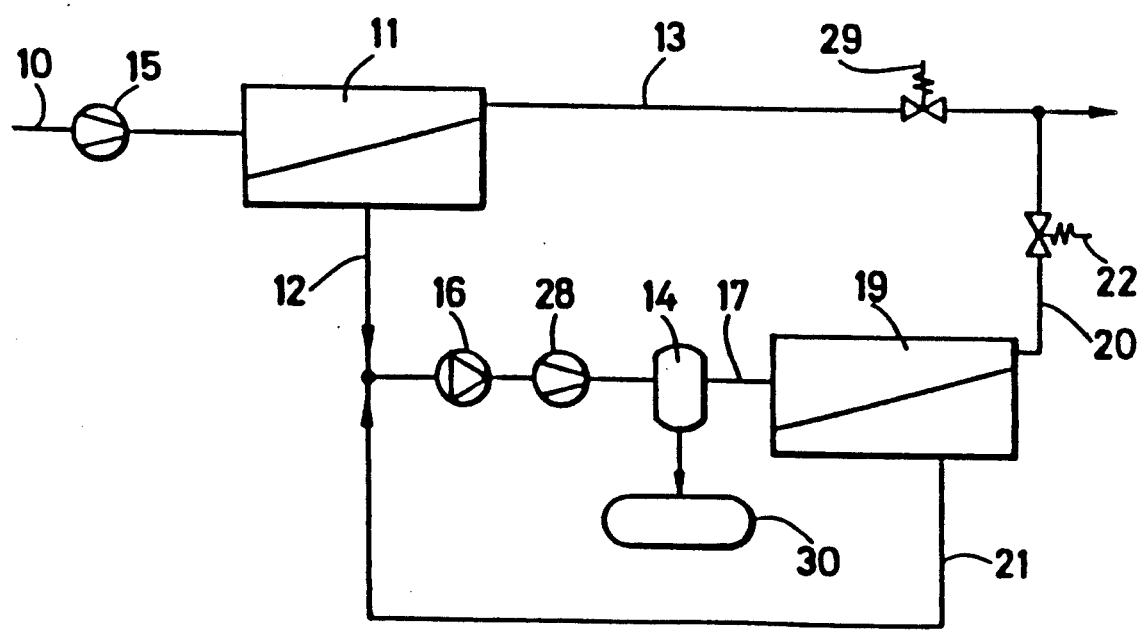
FIG. 2 is a view that shows a second exemplary embodiment for carrying out the inventive method.
Figure 3:
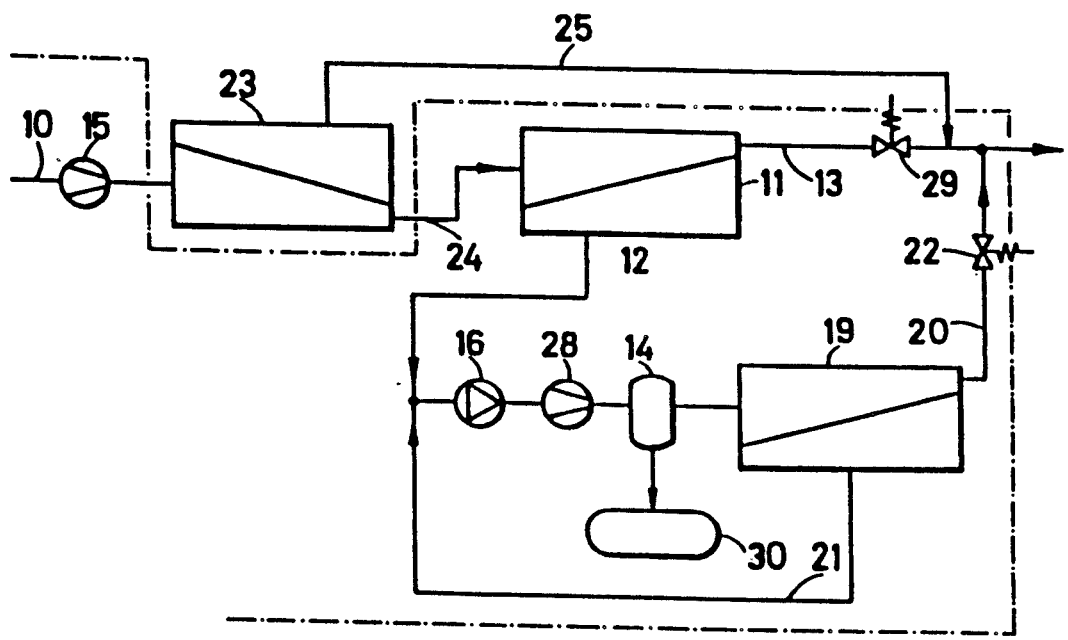
FIG. 3 is a view that shows a third exemplary embodiment of an arrangement for carrying out the inventive method.

In the arrangement illustrated in FIG. 3 for carrying out the method of the present invention, the arrangement indicated within the dot-dash line corresponds to the construction of the arrangement described in conjunction with FIG. 2, so that a description of this part of the arrangement of FIG. 3 can be obtained by reference to the description of the arrangement of FIG. 2. In the embodiment of FIG. 3, a third gas separation membrane device 23 is disposed in the stream of the air/permanent gas mixture 10 (untreated medium) between the compressor 15 and the first gas separation membrane device 11. This third gas separation membrane device 23 preferably allows oxygen to pass, so that a portion of the oxygen from the air/permanent gas mixture 10 (untreated medium) is separated off as an oxygen-rich gas stream 25 (oxygen filtrate). The oxygen-rich gas stream 25 is mixed with the organically depleted gas stream 13 of the first gas separation membrane device 11. The oxygen-depleted gas stream 24 of the third gas separation membrane device 23 is supplied to the first gas separation membrane device 11 as an (oxygen-depleted) air/permanent gas mixture, as described in conjunction with the embodiment of FIG. 2.

Figure 4:
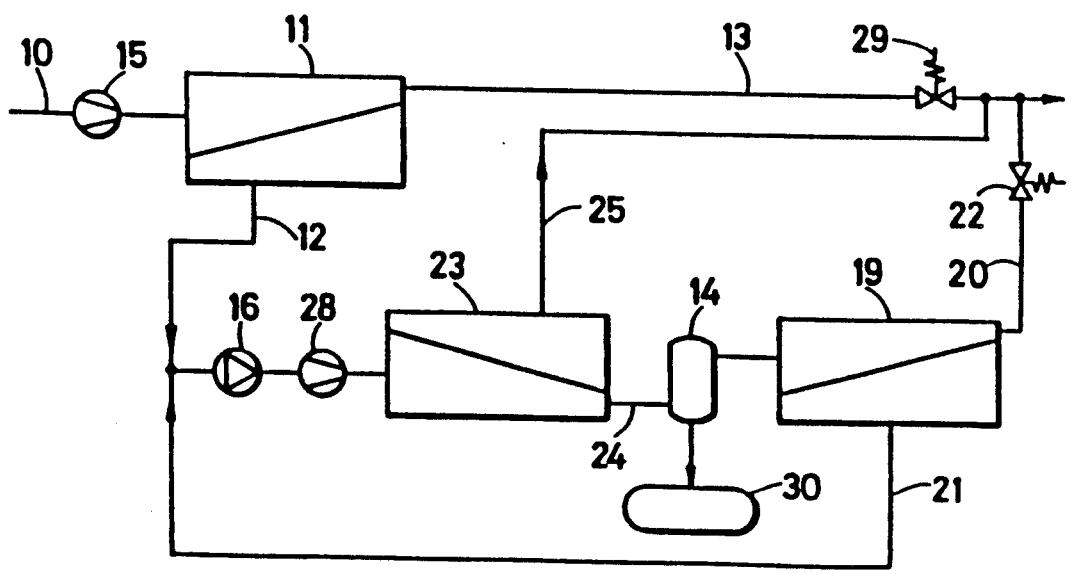
FIG. 4 is a view that shows a fourth exemplary embodiment of an arrangement for carrying out the inventive method.

The modified embodiment illustrated in FIG. 4 of an arrangement for carrying out the inventive method is basically of the same construction as the arrangement described in conjunction with FIG. 2. To this extent, reference is made to the description of the arrangement of FIG. 2. However, the embodiment of FIG. 4 differs from the arrangement illustrated in FIG. 2 in that a third gas separation membrane device 23 is inserted between the compressor 28 and the recovery device 14. In this embodiment also, the third gas separation membrane device 23 serves to deplete the oxygen from the gas streams 12 and 21 that are concentrated with organic compounds and come from the first gas separation membrane device 11 and the second gas separation membrane device 19. The oxygen-rich gas stream 25 from the third gas separation membrane device 23 is mixed with the gas stream 13 (retained gas) of the first gas separation membrane device 11 that is depleted of organic compounds. The oxygen-depleted gas stream 24 (oxygen retained gas) of the third gas separation membrane device 23 is supplied to the recovery device 14, as was described in conjunction with the illustration of the arrangement of FIG. 2. The arrangement illustrated in FIG. 4 can also be further modified by disposing the third gas separation membrane device 23 between the recovery device 14 and the second gas separation membrane device 19.

Figure 5:
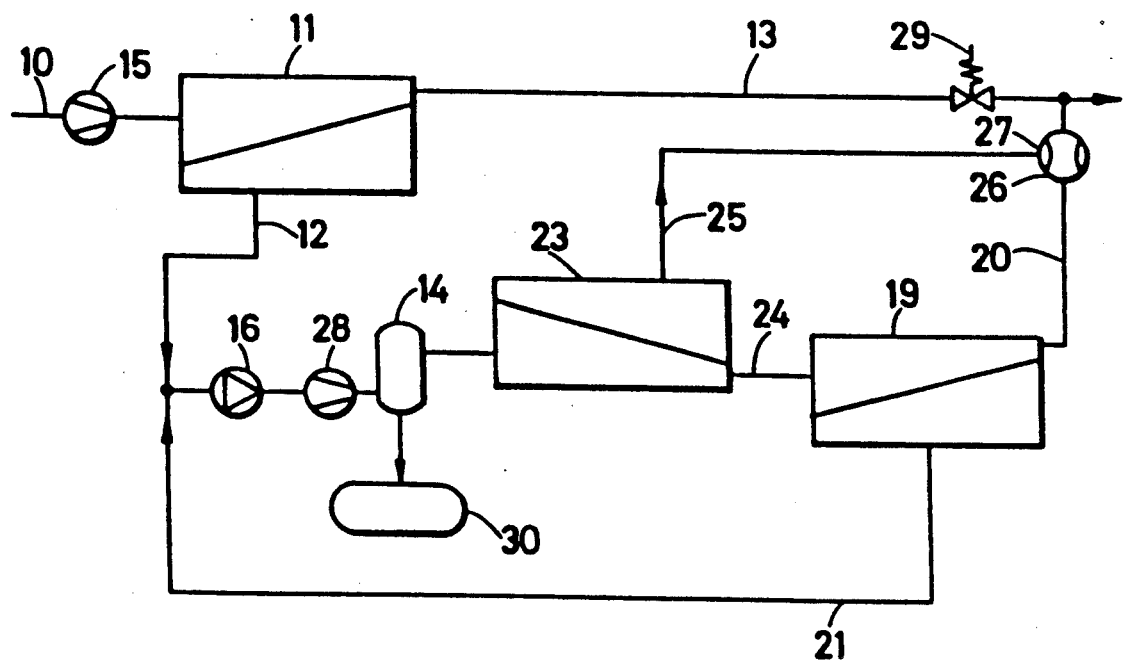
FIG. 5 is a view that shows a fifth exemplary embodiment of an arrangement for carrying out the inventive method.

The arrangement illustrated in FIG. 5 for carrying out the method of the present invention corresponds to the arrangement described in conjunction with FIG. 4 (modified form), whereby reference is made to the description of the embodiment of FIG. 4 with regard to the function thereof. The embodiment illustrated in FIG. 5 differs from that of FIG. 4 merely in that in place of the pressure regulator 22 in the depleted gas stream 20 of the second gas separation membrane device 19, a pump mechanism 26 is provided; this pump mechanism can be a jet pump for which the pressure of the depleted gas stream 20 (retained gas pressure) is used. The oxygen-rich gas stream 25 (oxygen filtrate) of the third gas separation membrane device 23 is conveyed to the intake or suction chamber of the pump mechanism 26, with the result that a partial vacuum is produced on the side of the oxygen-rich gas stream 25 (oxygen filtrate) of the third gas separation membrane device 23.

In principle, in order to carry out the inventive method pursuant to the aforementioned various arrangements any suitable pump mechanisms and compressors can be used. However, the compressors 15 and 18 are advantageously formed by fluid ring pumps, whereby the operating fluid of these pumps can be organic compounds via which a portion of the condensing components can be absorbed.

The first gas separation membrane device 11 and the second gas separation membrane device 19 advantageously use a polyetherimide composite membrane that preferably allows organic compounds to pass through. The third gas separation membrane device 23 advantageously uses an integrally asymmetrical polyetherimide membrane that preferably allows oxygen to pass through.

As already indicated in conjunction with the arrangement described in FIG. 1, the recovery device 14 for removing organic compounds from the organically concentrated gas stream can be operated using various physical procedures, such as pressure, removal of heat, sorption, or a combination of these procedures. The sorption itself can, in turn, be a physical absorption, a chemical absorption, or can be effected via adsorption. The removal of heat can be effected either directly or indirectly.

The arrangement described in conjunction with FIG. 2 for carrying out the inventive method was tested via a model computation. This showed a saving of the surface area of the membrane and a greater exhaust air purity. Selected as an example was a unit for recovering gasoline components from the exhaust air of fuel depots for fuels for internal reciprocating combustion engines, taking into consideration discharge limits for organic compounds. To recover the gasoline components, a pressure condensation at 10 bar was assumed.

TABLE 1

(Permeabilities or flux densities)
Gas permeability of polydimethylsiloxane (25°) in
$10^{-6} \cdot (m^3 \cdot m)/(m^2 \cdot h \cdot bar)$*

| Oxygen | Nitrogen | Propane | n-Butane | n-Pentane |
|---|---|---|---|---|
| 1.62 | 0.76 | 11.07 | 24.30 | 54.00 |

*General Electric Brochures, March 1982, "Permselective Membranes".

These values were confirmed for polyetherimide/silicone rubber composite membranes, with the temperature and pressure dependencies of the gasoline components also being measured.

Table 2 shows computations based on the construction of the inventive arrangement of FIG. 1 for carrying out the method of the present invention, while Table 3 shows computations based on the construction of the arrangement of FIG. 2 for carrying out the method of the present invention.

TABLE 4

Example of a membrane for oxygen separation.
Membrane type: integrally asymmetrical polyetherimide membrane

| Gas flow or flux 25 (°C.) | $N_2$ | $O_2$ | Methane | Ethane |
|---|---|---|---|---|
| $Nm^3/m^2 \cdot h \cdot bar$ | 0.00117 | 0.00932 | 0.00081 | 0.00051 |
| | Propane | | Butane | |
| | 0.00048 | | 0.00031 | |
| Selectivities | $O_2/C_1$ | $O_2/C_2$ | $O_2/C_3$ | $O_2/C_4$ |
| | 11.5 | 18.3 | 19.4 | 30.1 |

Figure 6:
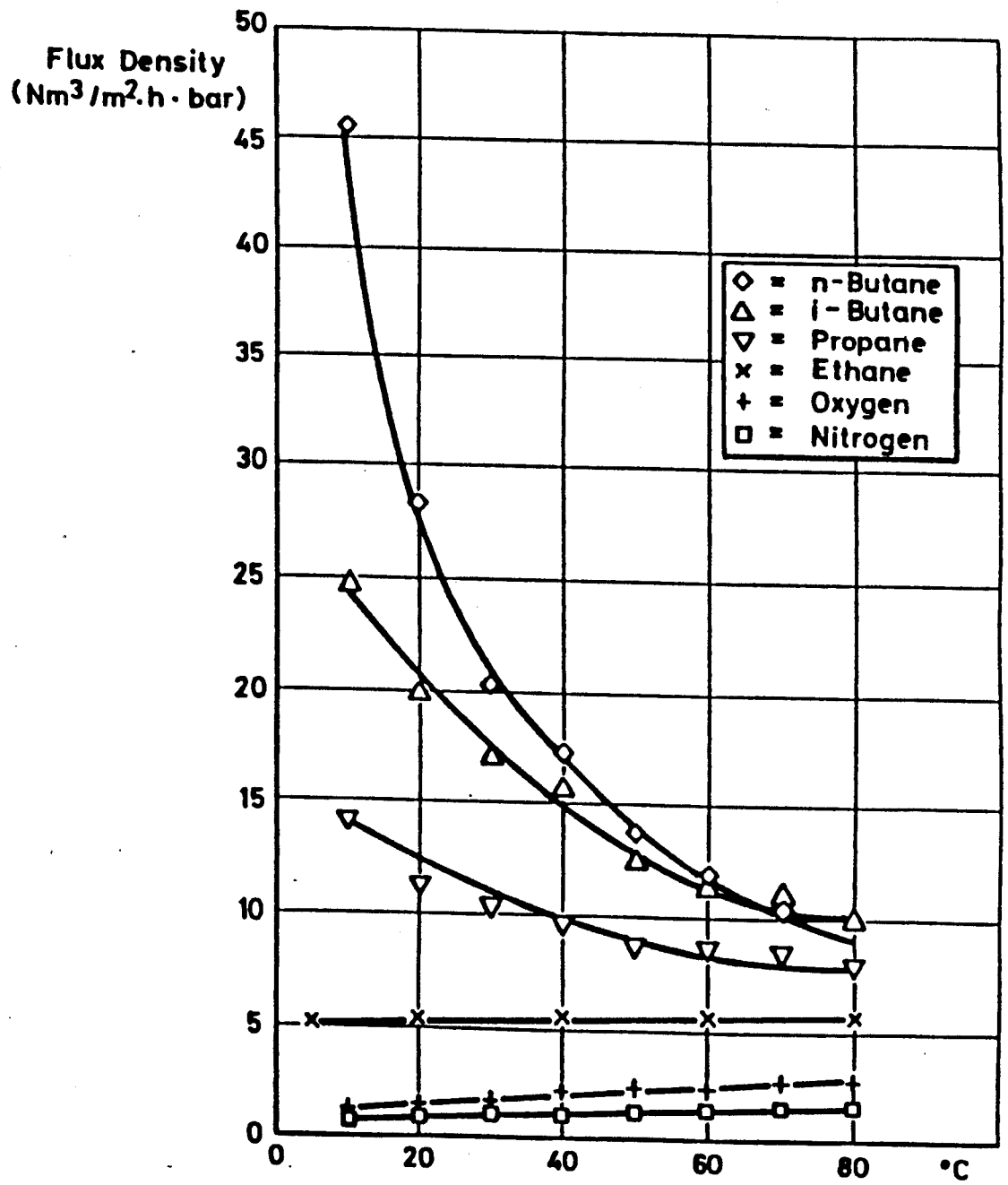
FIG. 6 is a view showing a graph in which the permeability of a membrane for various untreated medium components is plotted against temperature.
Figure 7:
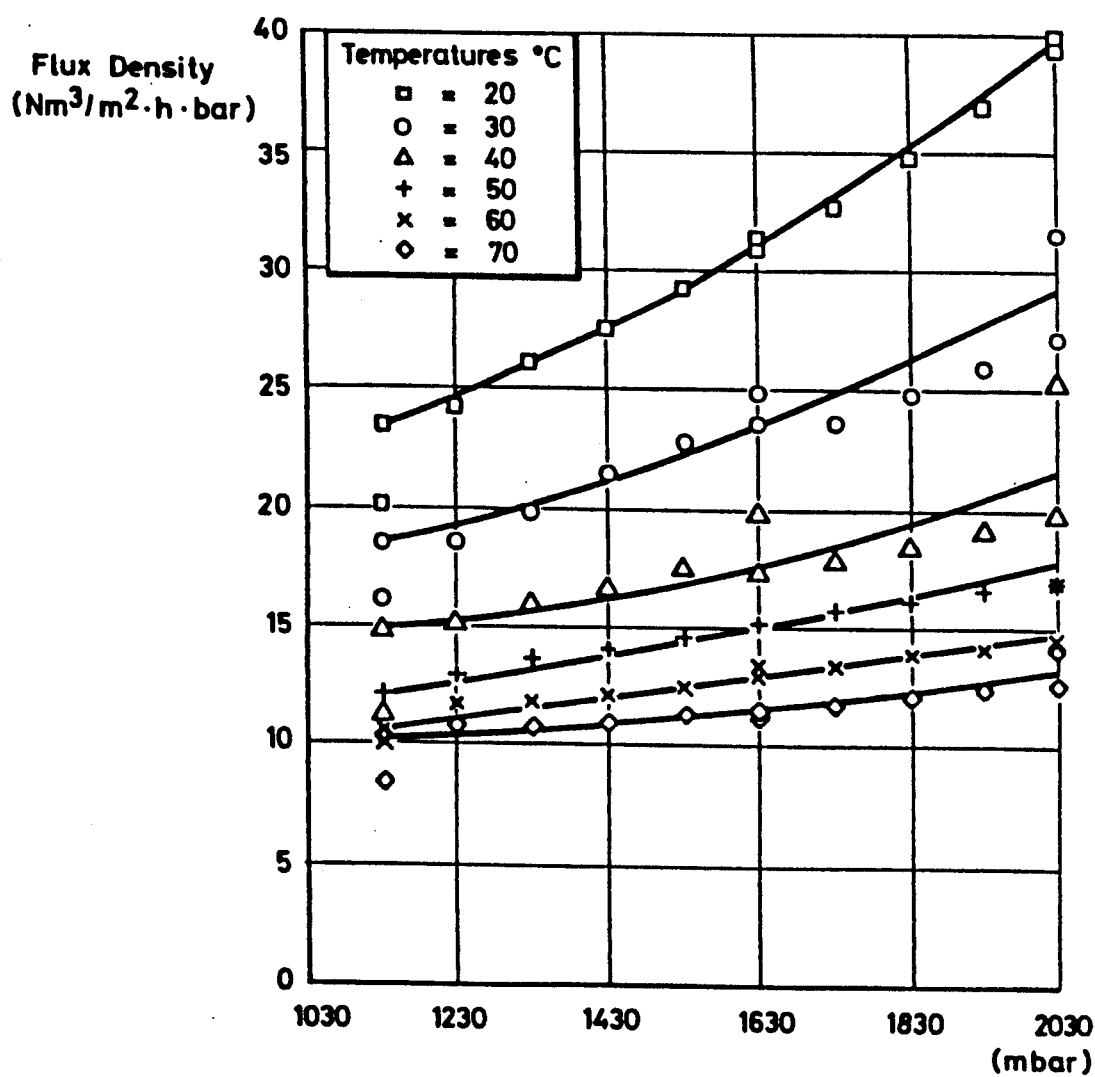
FIG. 7 is a view showing a graph in which the permeability of a membrane for n-butane is plotted against pressure at various temperatures.
Figure 8:
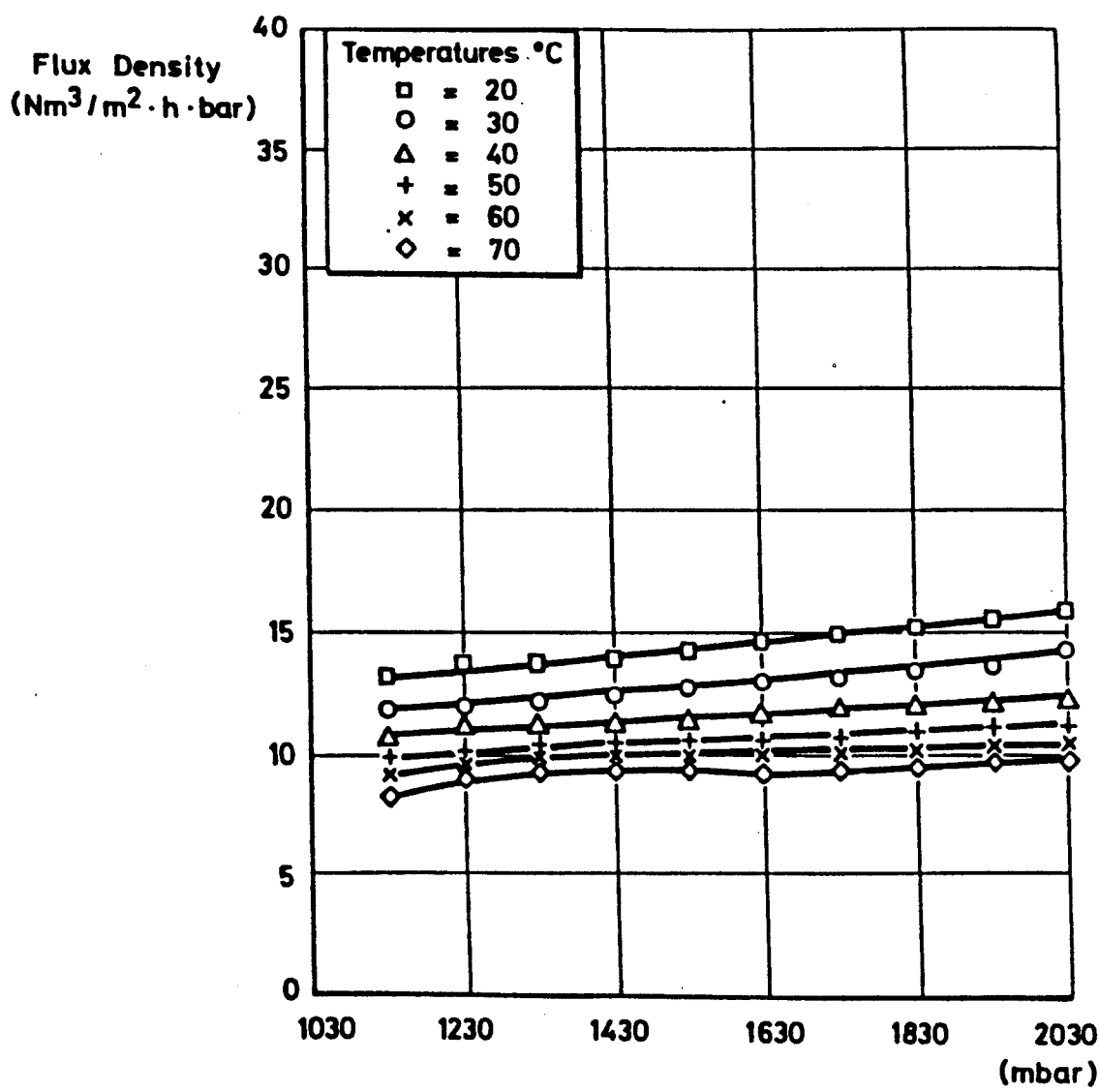
FIG. 8 is a view showing a graph in which the permeability of a membrane for propane is plotted against pressure at various temperatures.

In the graphs of FIGS. 6, 7, and 8, the permeation characteristics are plotted as a function of pressure and temperature for some of the main components of the gasoline vapor air mixtures.

In FIG. 6, actual gas measurements are plotted at different temperatures and the same inlet pressure. A strong dependency of the flux density upon the temperature is shown. Whereas for oxygen and nitrogen the flux density increases as the temperature rises, the flux densities for n-butane, i-butane, and propane decrease rapidly as the temperature rises. This graph shows that the operating temperature for a membrane separation unit should be between 20° C. and 40° C. so that an adequate separating capacity can be achieved with the membranes.

In FIGS. 7 and 8, the flux density of n-butane and propane are plotted against the inlet pressure at specific temperatures. These graphs show that the flux densities of propane and butane decrease as the pressure drops. In other words, the higher the partial pressure of the components n-butane and propane, the higher is the flux density. This characteristic was also measured for other main components, such as i-butane, i-pentane, and n-pentane.

Figure 9:
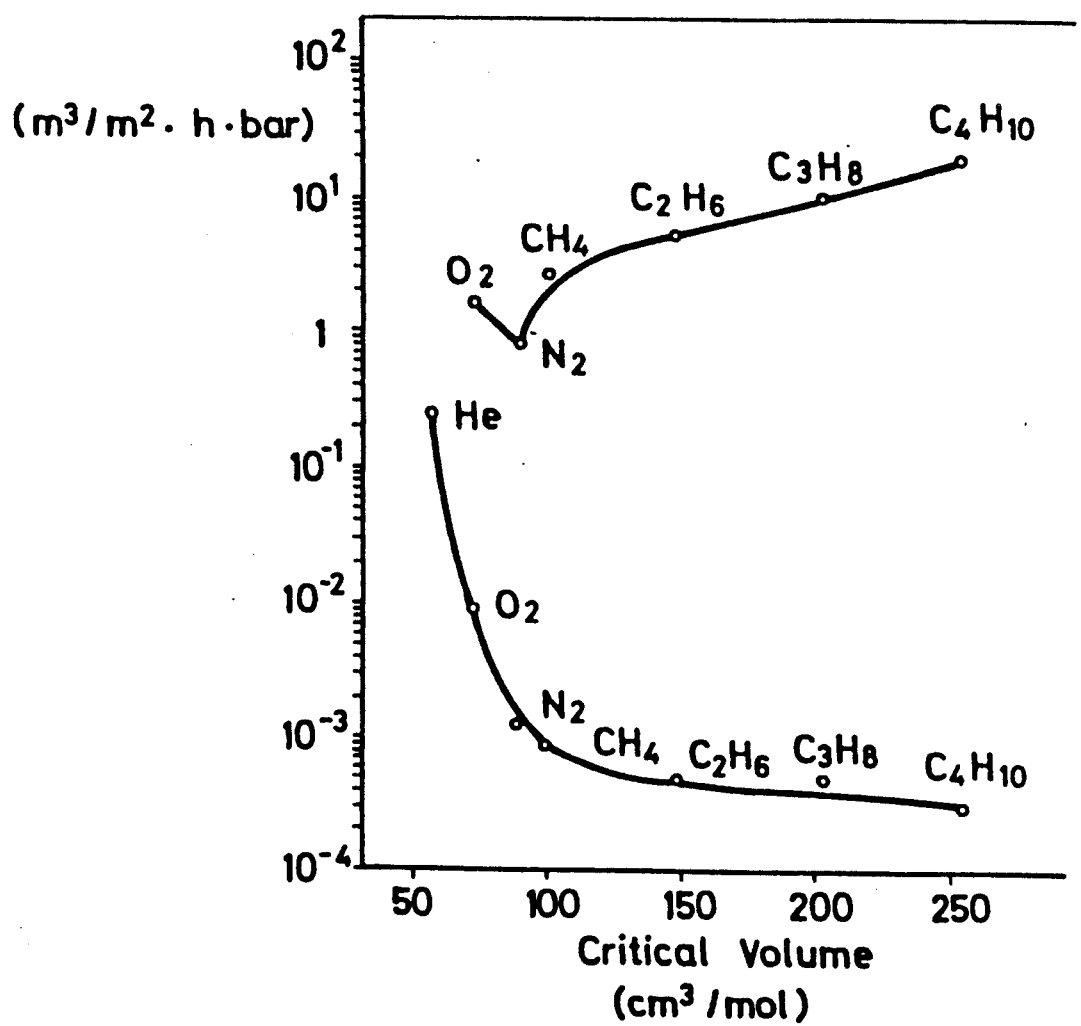
FIG. 9 is a view showing a graph showing the gas flux through two different gas separation membrane devices for explaining Table 4.

FIG. 9 serves to illustrate Table 4. Illustrated is the gas flux through two membrane types, an integrally asymmetric polyetherimide membrane and a silicone rubber composite membrane. The upper curve shows the permeation characteristics of the silicone rubber composite membrane, with hydrocarbon flux and low oxygen and nitrogen flux. The lower curve shows measured values for the integrally asymmetric polyetherimide membrane, with a high oxygen flux and low hydrocarbon fluxes.

With regard to the following Tables, it should be noted that with the described membranes, the gas flux L is a function of pressure, and is expressed by the following empirical equation:

$$L = L_o \times 10^{Exponent} \times p$$

with $L_o$ and Exponent being experimentally determined constants for the pertaining gas.

TABLE 2

| | Flux $L_o$ in $m^3/m \cdot h \cdot bar$ | Exponent in 1/bar | Vapor pressure in bar |
|---|---|---|---|
| Propane | 11.000 | 0.1700 | 10.9040 |
| i-Butane | 9.9000 | 0.6700 | 3.7600 |
| n-Butane | 9.9000 | 0.6700 | 2.8000 |
| i-Pentane | 21.0000 | 0.8100 | 1.1000 |
| n-Pentane | 21.0000 | 0.8100 | 0.8230 |
| Hexane-Octane | 20.0000 | 0.0000 | 0.2520 |
| Benzene/Toluene | 20.0000 | 0.0000 | 0.1610 |
| Oxygen | 1.3600 | 0.0000 | |
| Nitrogen | 0.6800 | 0.0000 | |
| Step surface area | 2.0000 $m^2$ | | |
| Membrane surface area | 120.0000 $m^2$ | Filtrate pressure | 0.2000 bar |
| | | Pressure ratio | 10.00 |
| | | Condensate pressure | 10.0000 bar |
| Inlet | 300.00 $m^3/h$ | | |
| Composition | 3.40% Propane | 6.00% | i-Butane |
| | 28.50% n-Butane | 4.90% | i-Pentane |
| | 3.90% n-Pentane | 4.80% | Hexane-Octane |
| | 0.60% Benzene/Toluene | 10.10% | Oxygen |
| | 37.80% Nitrogen | 0.00% | |
| Inlet (mixture) | 535.23 $m^3/h$ | | |
| Composition | 5.01% Propane | 5.26% | i-Butane |
| | 22.69% n-Butane | 3.20% | i-Pentane |
| | 2.46% n-Pentane | 2.79% | Hexane-Octane |
| | 0.34% Benzene/Toluene | 18.47% | Oxygen |
| | 39.76% Nitrogen | 0.00% | |
| Filtrate | 390.41 $m^3/h$ | | |
| Composition | 6.84% Propane | 7.17% | i-Butane |
| | 30.92% n-Butane | 4.39% | i-Pentane |
| | 3.37% n-Pentane | 3.83% | Hexane-Octane |
| | 0.47% Benzene/Toluene | 17.57% | Oxygen |
| | 25.46% Nitrogen | 0.00% | |
| Filtrate Composition after Condensation | 235.23 $m^3/h$ | | |
| | 7.07% Propane | 4.32% | i-Butane |
| | 15.29% n-Butane | 1.04% | i-Pentane |
| | 0.62% n-Pentane | 0.23% | Hexane-Octane |
| | 0.02% Benzene/Toluene | 29.15% | Oxygen |
| | 42.25% Nitrogen | 0.00% | |
| Retained | 144.80 $m^3/h$ | | |

TABLE 2-continued

| | | | |
|---|---|---|---|
| gas Composition | 0.09% Propane | 0.12% | i-Butane |
| | 0.53% n-Butane | 0.01% | i-Pentane |
| | 0.01% n-Pentane | 0.01% | Hexane-Octane |
| | 0.00% Benzene/Toluene | 20.91% | Oxygen |
| | 78.33% Nittogen | 0.00% | |
| Condensate | 10.06 m³/h Propane | 17.82 m³/h i-Butane | |
| | 84.73 m³/h Butane | 14.69 m³/h i-Pentane | |
| | 11.69 m³/h n-Pentane | 14.39 m³/h Hexane-Octane | |
| | 1.80 m³/h Benzene-Toluene | | |

TABLE 3

Crosscurrent process with subsequent condensation of miscible components

| | Flux $L_o$ in m³/m·h·bar | Exponent in 1/bar | Vapor pressure in bar |
|---|---|---|---|
| Propane | 11.0000 | 0.17001 | 0.9040 |
| i-Butane | 9.9000 | 0.6700 | 3.7600 |
| n-Butane | 9.9000 | 0.6700 | 2.8000 |
| i-Pentane | 21.0000 | 0.8100 | 1.1000 |
| n-Pentane | 21.0000 | 0.8100 | 0.8230 |
| Hexane-Octane | 20.0000 | 0.0000 | 0.2520 |
| Benzene-Toluene | 20.0000 | 0.0000 | 0.1610 |
| Oxygen | 1.3600 | 0.0000 | |
| Nitrogen | 0.6800 | 0.000 | |

Step Surface Area 0.5000 m²
Membrane Surface Area 15.0000 m²
Filtrate pressure 0.2000 bar
Pressure Ratio 50.00
Condensate pressure 10.0000 bar

| | | | |
|---|---|---|---|
| Inlet | 261.18 m³/h | | |
| Composition | 3.90% Propane | 6.89% | i-Butane |
| | 32.73% n-Butane | 5.63% | i-Pentane |
| | 4.48% n-Pentane | 5.51% | Hexane-Octane |
| | 0.69% Benzene-Toluene | 10.24% | Oxygen |
| | 29.93% Nitrogen | 0.00% | |
| Inlet (mixture) | 483.23 m³/h | | |
| Composition | 6.90% Propane | 6.65% | i-Butane |
| | 28.05% n-Butane | 3.74% | i-Pentane |
| | 2.84% n-Pentane | 3.14% | Hexane-Octane |
| | 0.39% Benzene-Toluene | 18.38% | Oxygen |
| | 29.91% Nitrogen | 0.00% | |
| Composition of inlet (mixture) after condensation | 326.99 m³/h | | |
| | 7.09% Propane | 4.33% | i-Butane |
| | 15.32% n-Butane | 1.04% | i-Pentane |
| | 0.62% n-Pentane | 0.23% | Hexane-Octane |
| | 0.02% Benzene-Toluene | 27.16% | Oxygen |
| | 44.20% Nitrogen | 0.00% | |
| Filtrate | 222.05 m³/h | | |
| Composition | 10.43% Propane | 6.38% | i-Butane |
| | 22.55% n-Butane | 1.52% | i-Pentane |
| | 0.91% n-Pentane | 0.34% | Hexane-Octane |
| | 0.03% Benzene-Toluene | 27.95% | Oxygen |
| | 29.89% Nitrogen | 0.00% | |
| Retained gas Composition | 104.93 m³/h | | |
| | 0.01% Propane | 0.00% | i-Butane |
| | 0.01% n-Butane | 0.00% | i-Pentane |
| | 0.00% n-Pentane | 0.00% | Hexane-Octane |
| | 0.00% Benzene-Toluene | 25.48% | Oxygen |
| | 74.50% Nitrogen | 0.00% | |
| Condensate | 10.18 m³/h Propane | 17.99 m³/h i-Butane | |
| | 85.47 m³/h n-Butane | 14.70 m³/h i-Pentane | |
| | 11.70 m³/h n-Pentane | 14.39 m³/h Hexane-Octane | |
| | 1.80 m³/h Benzene-Toluene | | |

Flux in m³/m·h·bar, Exponent in 1/bar:

| | | | | | |
|---|---|---|---|---|---|
| Propane | 11.0000 | 0.1700 | i-Butane | 9.9000 | 0.6700 |
| n-Butane | 9.9000 | 0.6700 | i-Pentane | 21.0000 | 0.8100 |
| n-Pentane | 21.0000 | 0.8100 | Hexane-Octane | 20.0000 | 0.0000 |
| Benzene-Toluene | 20.0000 | 0.0000 | Oxygen | 1.3600 | 0.0000 |
| Nitrogen | 0.6800 | 0.0000 | | 0.0000 | 0.0000 |

Step surface area 2.0000 m²
Membrane surface area 80.0000 m²
Filtrate pressure 0.2000 bar
pressure ratio 10.00

| | | | |
|---|---|---|---|
| Inlet | 300.00 m³/h | | |
| Composition | 3.40% Propane | 6.00% | i-Butane |
| | 28.50% n-Butane | 4.90% | i-Pentane |

TABLE 3-continued

| | | | |
|---|---|---|---|
| | 3.90% n-Pentane | 4.80% | Hexane-Octane |
| | 0.60% Benzene-Toluene | 10.10% | Oxygen |
| | 37.80% Nitrogen | 0.00% | |
| Filtrate | 261.44 m³/h | | |
| Composition | 3.90% Propane | 6.88% | i-Butane |
| | 32.70% n-Butane | 5.62% | i-Pentane |
| | 4.48% n-Pentane | 5.51% | Hexane-Octane |
| | 0.69% Benzene-Toluene | 10.25% | Oxygen |
| | 29.98% Nitrogen | 0.00 | |
| Retained gas Composition | 38.56 m³/h | | |
| | 0.01% Propane | 0.01% | i-Butane |
| | 0.04% n-Butane | 0.00% | i-Pentane |
| | 0.00% n-Pentane | 0.00% | Hexane-Octane |
| | 0.00% Benzene-Toluene | 9.11% | Oxygen |
| | 90.84% Nitrogen | 0.00% | |

The present invention is, of course, in no way restricted to the specific disclosure of the specification and drawings, but also encompasses any modifications within the scope of the appended claims.

What we claim is:

1. In a method of removing organic compounds from a primary air/permanent gas mixture, including conveying said air/permanent gas mixture which is initially untreated medium, to a first gas separation membrane means and dividing said mixture into a filtrate gas stream that is concentrated with organic compounds and a retained gas stream that is depleted of organic compounds, with said concentrated filtrate gas stream being conveyed to a recovery device for the recovery of said organic compounds therefrom, and with a gas stream exiting said recovery device, the improvement in combination therewith comprising the steps of:

effecting said recovery of said organic compounds from said concentrated filtrate gas stream in said recovery device by at least one recovery step undertaken selectively and preferably by condensing under pressure and optionally by removal of heat therefrom or by sorption;

then first raising the pressure of said primary air/permanent gas mixture directly prior to entry thereof into said first gas separation membrane means;

thereafter reducing the pressure of said concentrated filtrate gas stream after exit thereof from said first gas separation membrane means;

then discharging said depleted gas stream from said first gas separation membrane means into the atmosphere; and finally returning said gas stream that exits from said recovery device, at least in part, to at least some portion of said primary air/permanent gas mixture at a point subsequent to said pressure increase thereof.

2. A method in combination according to claim 1, in which said gas stream that exits from said recovery device is conveyed to said air/permanent gas mixture immediately prior to entry of said mixture into said first gas separation membrane means.

3. A method in combination according to claim 2, which includes the step of reducing the pressure of said gas stream that exits from said recovery device.

4. A method in combination according to claim 1, which includes the step of conveying said gas stream that exits from said recovery device to a second gas separation membrane means, which divides this gas stream into a depleted gas stream that is discharged into the atmosphere and a concentrated gas stream that is combined directly with said concentrated filtrate gas stream that exits said first gas separation membrane means.

5. A method in combination according to claim 4, which includes the step of providing means to adjust the pressure of said depleted gas stream that leaves said second gas separation membrane means in order to set the pressure thereof.

6. A method in combination according to claim 4, which includes the step of conveying said air/permanent gas mixture, after the pressure thereof has been raised, to a third gas separation membrane means, which divides said mixture into an oxygen-depleted gas stream that is conveyed into said first gas separation membrane means and an oxygen-rich gas stream that is discharged into the atmosphere, with said third gas separation membrane means having increased oxygen-passing characteristics.

7. A method in combination according to claim 4, which includes the step of conveying said concentrated filtrate gas stream from said first gas separation membrane means, prior to entry of this gas stream into said recovery device, to a third gas separation membrane means, which divides this gas stream into an oxygen-depleted gas stream that is conveyed to said recovery device and an oxygen-rich gas stream that is discharged into the atmosphere, with said third gas separation membrane means having increased oxygen-passing characteristics.

8. A method in combination according to claim 4, which includes the step of conveying said gas stream that exits from said recovery device, prior to entry of this gas stream into said second gas separation membrane means, to a third gas separation membrane means, which divides this gas stream into an oxygen-depleted gas stream that is conveyed to said second gas separation membrane means and an oxygen-rich gas stream that is discharged into the atmosphere, with said third gas separation membrane means having increased oxygen-passing characteristics.

9. A method in combination according to claim 8, which includes the steps of: providing a pump mechanism that has a suction side; utilizing said depleted gas stream that exits said second gas separation membrane means to drive said pump mechanism prior to said discharge of this gas stream into the atmosphere; and conveying said oxygen-rich gas stream of said third gas separation membrane means to said suction side of said pump mechanism to generate a partial vacuum relative to said oxygen-rich gas stream.

10. A method in combination according to claim 1, which includes the step of increasing the pressure of said reduced-pressure concentrated filtrate gas stream from said first gas separation membrane means prior to entry of this gas stream into said recovery device.

11. A method in combination according to claim 1, which includes the step of reducing the pressure of said depleted gas stream after exit thereof from said first gas separation membrane means.

12. A method in combination according to claim 1, which includes the step of effecting said recovery of said organic compounds from said concentrated filtrate gas stream in said recovery device by removal of heat therefrom.

13. A method in combination according to claim 1, which includes the step of effecting said recovery of said organic compounds from said concentrated filtrate gas stream in said recovery device by sorption selected from the group consisting of physical absorption, chemical absorption, and adsorption.

14. A method in combination according to claim 1, in which said gas separation membrane means includes a polyetherimide composite membrane.

15. A method in combination according to claim 1, in which said gas separation membrane means includes an asymmetrical polyetherimide membrane.

16. A method in combination according to claim which includes the step of making said air/permanent gas mixture inert prior to said step of raising the pressure, thereof.

17. A method in combination according to claim 1, which includes the step of conveying said concentrated filtrate gas stream from said first gas separation membrane means, prior to entry of this gas stream into said recovery device, to a further gas separation membrane means, which divides this gas stream into a depleted gas stream that is discharged into the atmosphere and a concentrated gas stream that is conveyed to said recovery device.

18. A method according to claim 1, which includes the step of effecting said recovery of said organic compounds from said concentrated filtrate gas stream in said recovery device by condensation under pressure.

* * * * *